United States Patent [19]
Hughes

[11] Patent Number: 5,989,207
[45] Date of Patent: Nov. 23, 1999

[54] DOUBLE SWIRL STENT

[76] Inventor: Boyd R. Hughes, 1469 Stacy Dr., Blg. 29, Canton, Mich. 48188-1401

[21] Appl. No.: 08/962,634

[22] Filed: Nov. 3, 1997

[51] Int. Cl.$^6$ .................................. A61M 5/00; A61F 2/04
[52] U.S. Cl. .................................................... 604/8; 623/12
[58] Field of Search .............................. 604/8–9, 27, 43, 604/106, 523, 540, 93, 264; 600/29; 623/1, 11, 12, 66

[56] References Cited

U.S. PATENT DOCUMENTS

| | | |
|---|---|---|
| 4,230,115 | 10/1980 | Walz, Jr. et al. . |
| 4,710,169 | 12/1987 | Christopher . |
| 4,740,207 | 4/1988 | Kreamer . |
| 5,112,306 | 5/1992 | Burton et al. . |
| 5,147,385 | 9/1992 | Beck et al. . |
| 5,192,310 | 3/1993 | Herweck et al. . |
| 5,197,996 | 3/1993 | Reid et al. . |
| 5,295,979 | 3/1994 | DeLaurentis et al. . |
| 5,306,226 | 4/1994 | Salama . |
| 5,411,550 | 5/1995 | Herweck et al. . |
| 5,501,669 | 3/1996 | Conway et al. . |
| 5,507,786 | 4/1996 | Morgan et al. . |
| 5,514,178 | 5/1996 | Torchio . |

*Primary Examiner*—Corrine McDermott
*Assistant Examiner*—Patricia Bianco
*Attorney, Agent, or Firm*—Dykema Gossett PLLC

[57] ABSTRACT

A stent that is intended to be introduced into a human person has an elongated one-piece body with an outer wall of generally uniform thickness and with an exterior cylindrical surface. The body has a first longitudinally extending axis forming the center line for the cylindrical surface. A tubular passage is located within the interior of the body and has a second longitudinal axis which is parallel to and spaced from the first longitudinal axis. The passage has a generally cylindrical wall formed in part by the outer wall of the body. An elongated channel is located within the interior of the body and partially enclose the generally cylindrical wall of the tubular passage. The outer wall has an entrance slot therein for opening the channel. The slot is spaced from the cylindrical wall of the tubular passage. The passage, channel and slot each extending the entire length of the body.

18 Claims, 3 Drawing Sheets

DOUBLE SWIRL STENT

BACKGROUND OF THE INVENTION

The present invention relates generally to a stent suitable for insertion within the human body and, more particularly, to a blockage resistant stent used to increase the flow of fluid between two areas of the body.

Commonly, stents are used for many applications in the human body. One application, for example, is insertion of a stent within an artery to increase the blood flow within the artery. The stent in such a case may be used to prevent the artery from closing after surgery.

Stents may also be used to increase the flow of urine from the bladder in the presence of kidney stones. Stents are commonly inserted into the ureter to hold open the entrance of the bladder. Most stents are single passage stents. One drawback to such stents is that kidney stones or other foreign matter tends to clog the stent and prevent from the flow of fluid through the stent. Once the stent has been clogged, the stent must be cleared. In certain circumstances the stent must be replaced. Both actions require uncomfortable procedures and increase the medical bills associated therewith.

SUMMARY OF THE INVENTION

It is therefore a feature of the invention to provide a stent that resists blockage after insertion into the person.

In one aspect, the present invention has an elongated one-piece body having an outer wall of a generally uniform thickness with an exterior cylindrical surface. The body has a first longitudinally extended axis forming the center line for the cylindrical surface. A tubular passage is located within the interior of the body and has a second longitudinally extending axis which is parallel to and spaced apart from the first longitudinal axis. The passage has a generally cylindrical wall formed in part by the outer wall of the body and an elongated channel within the interior of the body which partially encloses the generally cylindrical wall of the tubular passage. The outer wall has an entrance slot therein for opening the channel. The slot is spaced from the cylindrical wall of the tubular passage. The passage, channel and slot each extend the entire length of the body.

One advantage of the invention is that the tubular passage of the stent may be used to carry medication through the stent.

Another advantage of the invention is that the longitudinal slot on the outer wall of the body of the stent may be pinched together to make the outer diameter of the stent narrower during insertion of the stent. This makes the stent easier to insert into the narrow passages of the human body.

Yet another advantage of the present invention is that the groove allows kidney stones to pass through the stent while urine continues to flow through the tubular passage.

BRIEF DESCRIPTION OF THE DRAWINGS

Other features and advantages of the present invention will become apparent in the following detailed description which should be read in conjunction with the drawings in which.

DETAILED DESCRIPTION OF THE PREFERRED EMBODIMENT

Figure 1:
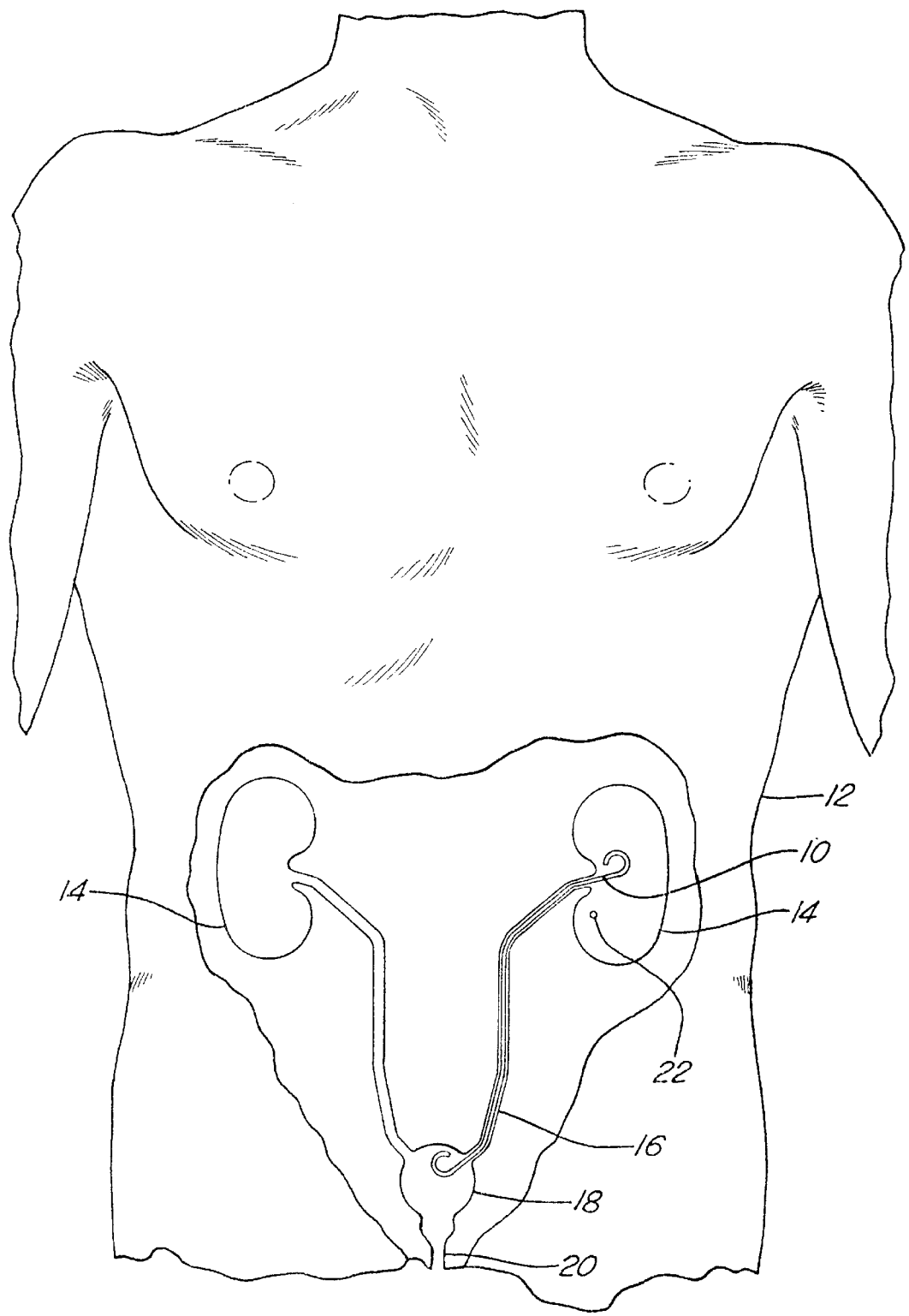
FIG. 1 is a cutaway view of a person having a stent according to the present invention inserted between the bladder and kidneys.

In the following figures, like reference numerals will be used to represent like components. The figures illustrate a stent inserted between a kidney and a bladder and in an artery near a heart. However, other locations suitable for the stent would be evident to those skilled in the art.

Referring now to FIG. 1, a stent 10 is inserted within a human 12. Human 12 has kidneys 14, a ureter 16 and a bladder 18. Ureter 16 connects each kidney 14 to bladder 18. Urethra 20 channels fluid from bladder 18 out of human 12.

Stones 22 may form in kidney 14. Stones 22 have a tendency to get lodged in ureter 16 when they pass out of kidney 14. Ureter 16 has three narrow points that may lodge a stone 22. The first is at the ureteropelvic junction; the second is at the crossing with the iliac vessels; and the third is where the ureter 16 penetrates bladder 18. Stent 10 when inserted in ureter 16 permits stones 22 to pass easily between kidney 14 and bladder 18 without becoming lodged in the narrow portions of ureter 16.

Figure 2:
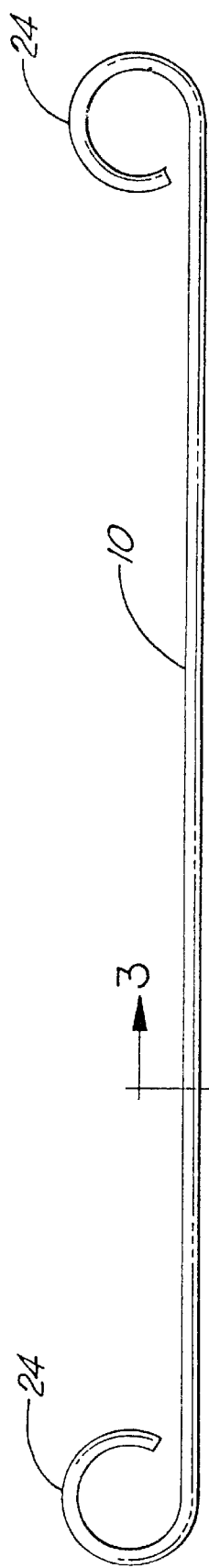
FIG. 2 is a side view of a stent according to the present invention.

Referring now to FIG. 2, stent 10 preferably has a uniform cross-section throughout its length. Stent 10 preferably has curved ends 24. The desired length of stent 10 depends on the particular application for which stent 10 is introduced. If, for example, stent 10 is used in ureter 16, stent 10 has a length extending into kidney 14 and bladder 18.

Stent 10 is preferably formed of a flexible polymer material. The polymeric material may, for example, be a clear plastic material. The polymeric material such as polytetrafloroethylene, Dacron®, synthetic polyester fibers, polyurethane, or silicon elastomer fibers may be used. It is also preferred that the outside of stent 10 be coated with a coating. Coating may be hydrophillic or be made of polytetrafloroethylene. Of course, by varying the material and choosing appropriate molecular weights, degrees of crystallinity and/or expansion parameters for the polymer matrix, the permeability and rigidity and of stent 10 may be altered.

Figure 3:
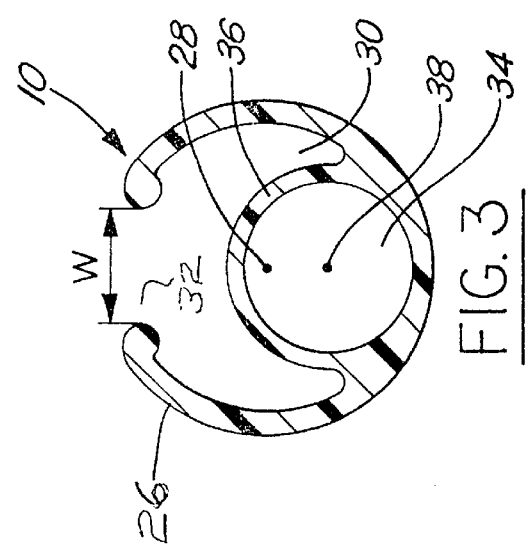
FIG. 3 is a cross-sectional view taken along line 3—3 of FIG. 2.
Figure 4:
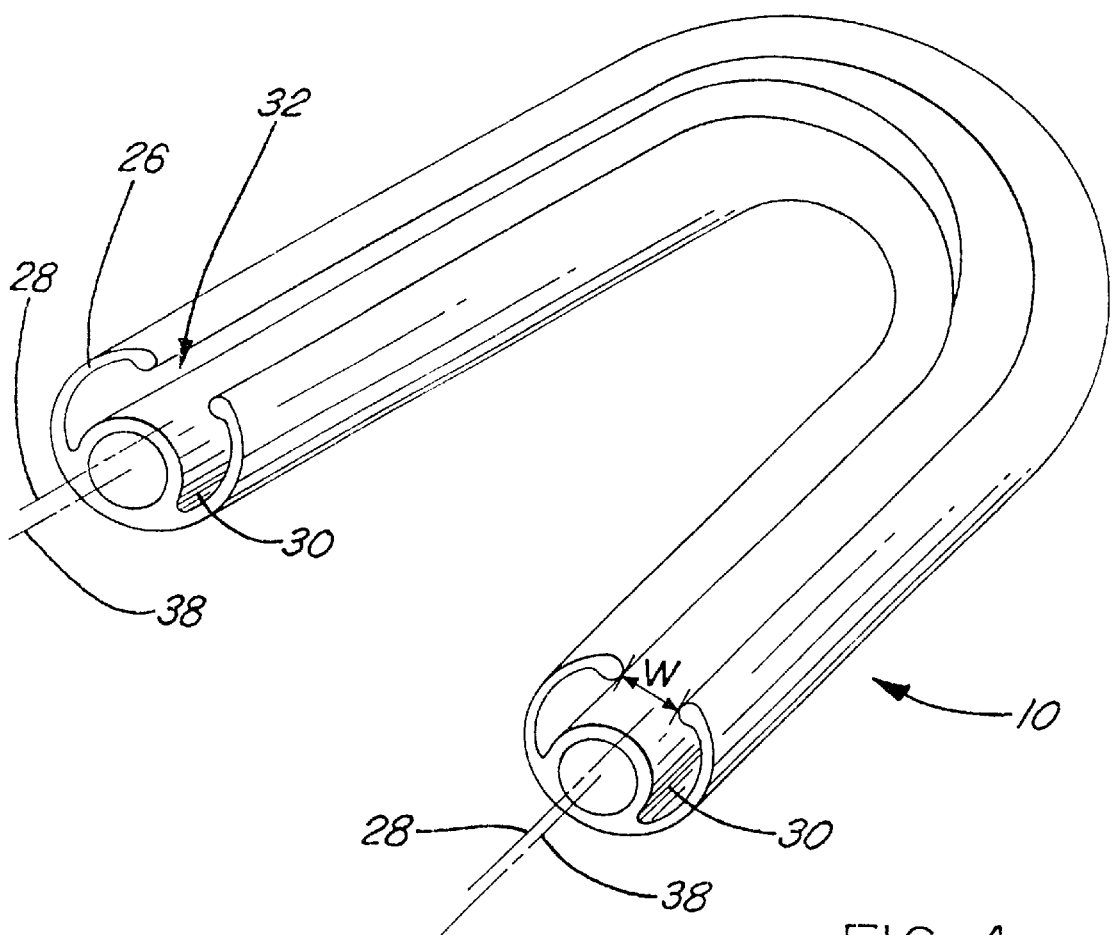
FIG. 4 is a perspective view of a stent according to the present invention.

Referring now to FIGS. 3 and 4, stent 10 has an outer wall 26. Outer wall 26 generally defines an exterior cylindrical surface. In one constructed embodiment outer wall 26 defines stent 10 having a diameter of 8 French (about 0.105 inches). Outer wall 26 has a longitudinal axis 28 which defines the center of the cylindrical surface of outer wall 26. Outer wall 26 defines an elongated channel 30 therein. Elongated channel has a generally semi-circular shape. Elongated channel 30 preferably extends the length of the body of stent 10. Outer wall 26 has a slot 32 extending therethrough. Slot 32 is an opening in outer wall 26. In one constructed embodiment, slot 32 has a width W of 0.04 inches. Slot 32 is capable of becoming smaller to reduce the diameter of stent 10 during insertion into the body.

A separate tubular passage 34 from channel 30 is contained within outer walls 26. Tubular passage 34 has a cylindrical wall 36 partially defining tubular passage 34. A portion of outer wall 26 also forms tubular passage 34. Tubular passage 34 is generally cylindrical in shape and has a longitudinal axis 38. Each of outer wall 26 and cylindrical wall 36 are preferably about 0.01 inches thick. The intersection between cylindrical wall 36 and outer wall 26 is preferably rounded to eliminate a sharp edge therebetween. Also, the portion of outer walls 26 adjacent slot 32 are also preferably rounded to eliminate any sharp edges.

Elongated channel 30 preferably has a greater cross sectional area than tubular passage 34. Elongated channel 30 thus may easily allow kidney stones or other foreign particles to pass therethrough.

Figure 5:
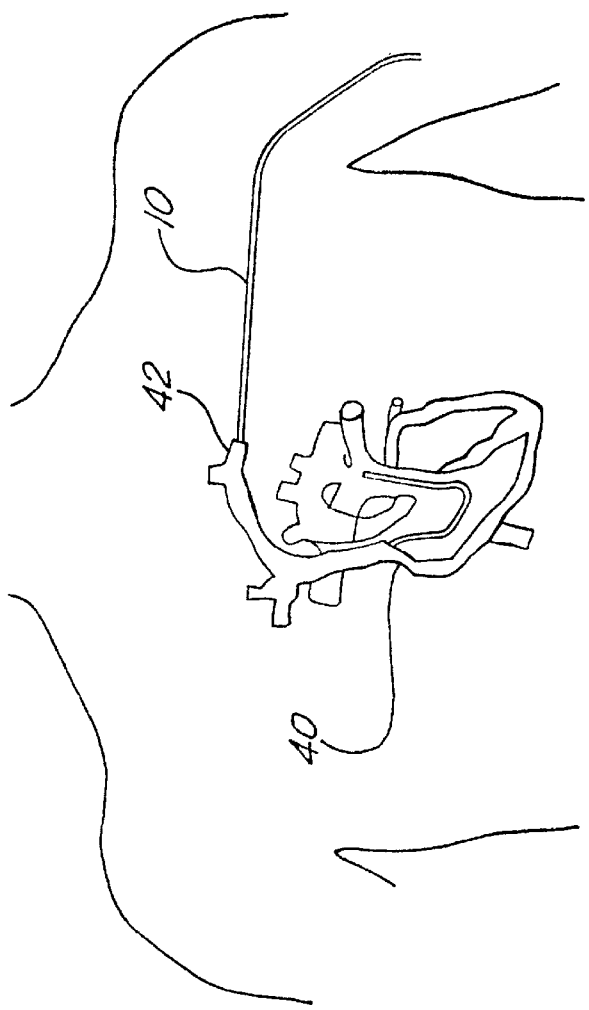
FIG. 5 is a cutaway view of a stent inserted within an artery near the heart of a human.

Referring now to FIG. 5, a heart 40 is shown in a human 12 having an artery 42 leading thereto. A stent 10 is shown inserted into artery 42 in much the same manner as that of FIG. 1. Tubular passage 34 may be used to pass medicine to heart 40.

In operation, a catheter or other tool may be used to insert stent 10 within human 12. The tool may slightly collapse slot 32 to temporarily reduce the diameter of outer walls 26 during insertion of stent 10 by partially reducing the width W of slot 32. Upon removing the tool, slot 32 again opens and outer walls 26 moved back to their original position.

Kidney stones pass through elongated channel 30 while urine is allowed to flow through tubular passage 34. If medicines are desired to be directed to the place where stent 10 has been inserted, medicine may be injected through tubular passage 34.

Stent 10 is designed to remain inserted within the body for as long as required or up to about 3 to 4 months. Commonly, a stent would not remain in a person longer than 4 months.

It should be understood by those skilled in the art that variations and modifications to the preferred embodiments described above may without departing from the true scope of the invention as defined by the following claims:

What I claim is:

1. A stent intended to be introduced into a human person comprising:
    an elongated one-piece body having an outer wall of generally uniform thickness and with an exterior cylindrical surface;
    said body having a first longitudinally extending axis forming the center line for said cylindrical surface;
    a tubular passage located within the interior of said body and having a second longitudinal axis which is parallel to and spaced from said first longitudinal axis;
    said tubular passage formed in part by the outer wall of said body and in part by a cylindrical wall;
    an elongated channel within the interior of said body and partially enclosing said cylindrical wall of said tubular passage;
    said outer wall having an entrance slot therein for opening said channel;
    said slot being spaced from the cylindrical wall of said tubular passage; and
    said passage, channel and slot each extending the entire length of said body;
    said channel having a cross-sectional area which is larger than the cross-sectional area of said tubular passage.

2. The stent defined in claim 1, wherein said tubular body is made from a clear plastic material.

3. The stent defined in claim 2, wherein said plastic material is polyurethane.

4. The stent defined in claim 2, wherein said plastic material is provided with a hydrophillic coating throughout its length.

5. The stent defined in claim 2, wherein said plastic material is provided with a polytetrafloroethylene coating throughout its length.

6. The stent defined in claim 1, wherein said tubular body is of uniform cross-section throughout its length.

7. The stent defined in claim 1, wherein said body has a pair of end portions which are curved.

8. The stent defined in claim 1, wherein said tubular passages is opened at both ends for introducing into the human person a medicine which is delivered through said tubular passage.

9. The stent defined in claim 1, wherein said body is of sufficient length to extend from the kidney to the bladder area after insertion into the human person.

10. The stent defined in claim 1, wherein said body is of sufficient length to permit it to be inserted through the arm and chest area into the heart area for introducing medication through the tubular passage to the human person and for removing blockages of foreign matter through the elongated slot and channel.

11. A stent intended to be introduced into a human person having a kidney, a bladder and a ureter extending between the kidney and the bladder, the stent comprising:
    an elongated one-piece body having an outer wall of generally uniform thickness and with an exterior cylindrical surface;
    said body having a first longitudinally extending axis forming the center line for said cylindrical surface;
    said body having a length greater than the ureter so that the body extends into the bladder and the kidney;
    a tubular passage located within the interior of said body and having a second longitudinal axis which is parallel to and spaced from said first longitudinal axis;
    said tubular passage formed in part by the outer wall of said body and in part by a cylindrical wall;
    an elongated channel within the interior of said body and partially enclosing said cylindrical wall of said tubular passage;
    said outer wall having an entrance slot therein for opening said channel;
    said slot being spaced from the cylindrical wall of said tubular passage, said slot capable of varying from a first width to a second width; and
    said passage, channel and slot each extending the entire length of said body;
    said channel having a cross-sectional area which is larger than the cross-section area of said tubular passage.

12. The stent defined in claim 11, wherein said tubular body is made from a clear plastic material.

13. The stent defined in claim 12, wherein said plastic material is polyurethane.

14. The stent defined in claim 12, wherein said plastic material is provided with a hydrophillic coating throughout its length.

15. The stent defined in claim 12, wherein said plastic material is provided with a polytetrafloroethylene coating throughout its length.

16. The stent defined in claim 11, wherein said tubular body is of uniform cross-section throughout its length.

17. The stent defined in claim 11, wherein said body has a pair of end portions which are curved.

18. The stent defined in claim 11, wherein said tubular passages is opened at both ends for introducing into the human person a medicine which is delivered through said tubular passage.

* * * * *